United States Patent [19]
Cadet et al.

[11] Patent Number: 5,625,140
[45] Date of Patent: Apr. 29, 1997

[54] ACOUSTIC ANALYSIS OF GAS MIXTURES

[75] Inventors: Gardy Cadet, Orange; Jorge L. Valdes, Bedminster, both of N.J.

[73] Assignee: Lucent Technologies Inc., Murray Hill, N.J.

[21] Appl. No.: 570,906

[22] Filed: Dec. 12, 1995

[51] Int. Cl.$^6$ ........................................... G01N 29/02
[52] U.S. Cl. ................................. 73/24.01; 73/597
[58] Field of Search ......................... 73/24.01, 61.49, 73/61.75, 61.79, 64.53, 597

[56] References Cited

U.S. PATENT DOCUMENTS

| | | | |
|---|---|---|---|
| 2,568,277 | 9/1951 | Eltgroth | 73/24.01 |
| 3,468,157 | 9/1969 | Burk et al. | 73/24.01 |
| 4,004,461 | 1/1977 | Lynnworth | 73/861.27 |
| 4,011,473 | 3/1977 | Massa | 310/335 |
| 4,520,654 | 6/1985 | Terhune | 73/24.01 |
| 4,576,047 | 3/1986 | Lauer et al. | 73/597 |
| 4,596,133 | 6/1986 | Smalling | 73/24.01 |
| 4,662,212 | 5/1987 | Noguchi et al. | 73/24.01 |
| 4,852,407 | 8/1989 | Komine et al. | 73/597 |
| 5,060,506 | 10/1991 | Douglas | 73/24.01 |
| 5,115,670 | 5/1992 | Shen | 73/61.41 |
| 5,247,826 | 9/1993 | Frola | 73/24.01 |
| 5,392,635 | 2/1995 | Cadet | 73/24.01 |

FOREIGN PATENT DOCUMENTS

| | | |
|---|---|---|
| 53453 | 12/1980 | European Pat. Off. . |
| 67068 | 12/1982 | European Pat. Off. . |
| 495538 | 7/1992 | European Pat. Off. . |
| 798323 | 7/1958 | United Kingdom ............ 73/24.01 |
| 2215049 | 9/1989 | United Kingdom . |
| 6703 | 11/1987 | WIPO . |
| 3724 | 3/1992 | WIPO . |

OTHER PUBLICATIONS

M. Kniazuk et al., "Ultrasonic Gas Analyzer", Instruments and Automation, vol. 28, Nov. 1955, pp. 1916–1917.

"A New Technique for te Preparation of Low–Loss and Graded–Index Optical Fibers", MacChesney, J.B. et al., Proceedings of the IEEE, pp. 1280–1281 (1974).

*Primary Examiner*—Hezron E. Williams
*Assistant Examiner*—Daniel S. Larkin
*Attorney, Agent, or Firm*—Richard J. Botos

[57] ABSTRACT

The present invention provides an acoustic cell for determining the composition of gas mixtures. The acoustic gas composition analysis cell has transducers isolated from the cell body by a metal housing. A sound-absorbing sleeve around the body of the transducer increases the signal-to-noise ratio to at least 4:1. Additionally, the transducers employed in the acoustic cell operate in the kilohertz range, reducing attenuation in the gas mixture being analyzed. The cell body employs vacuum seals which permit the use of the cell in line with vacuum equipment.

7 Claims, 6 Drawing Sheets

ACOUSTIC ANALYSIS OF GAS MIXTURES

BACKGROUND OF THE INVENTION

1. Field of the Invention

The invention relates to the field of acoustic gas monitoring and, more particularly, to the in-line monitoring and control of the composition of gas mixtures.

2. Description of the Related Art

In many manufacturing operations, accurate information concerning a reaction gas composition is necessary to control a particular process. For example, chemical vapor deposition (CVD) processes require precise gas mixtures to reliably create materials of a specific composition. Formation of semiconductor materials and optical fiber performs often involves incorporation of dopant materials in very small concentrations. The dopant material is supplied by a dopant precursor gas which is mixed with other deposition gases in a reaction chamber. Because of the low concentration used in the vapor deposition process, the dopant gas is usually mixed with a carrier gas to ensure an even distribution of dopant within the reaction chamber. The career gas must deliver a consistent quantity of the dopant gas. In-line gas monitoring is often used to ensure this consistent delivery.

Acoustic monitoring of gases can employ ultrasound, i.e., sound waves having a frequency ranging from a few kHz to 10 MHz. Acoustic techniques have been extensively used for gas flow monitoring. More recently, efforts have turned to developing acoustic cells and processes which can determine the concentration of a component of a binary gas mixture. In general, acoustic concentration analysis of a gas mixture is performed by measuring the speed with which sound waves propagate through a gas mixture. Because the speed at which the sound waves travel through a gas is related to molecular weight, the concentration of a component of a gas mixture can be accurately determined.

For a single component system under ideal conditions, the velocity of sound, $V_s$ can be obtained from the following equation:

$$V_s = \left( \frac{\gamma RT}{M} \right)^{1/2}$$

where $\gamma$ is the specific heat capacity ratio ($C_p/C_v$), R is the universal gas constant (8.3143 J/mol K.), T is the absolute temperature in degrees Kelvin, and M is the molecular weight of the gas in kg.

In the case of a binary gas mixture, a similar relationship exists, with $\gamma$ and M replaced by $\bar{\gamma}$ and $\bar{M}$. The acoustic velocity of a binary gas mixture is then represented by:

$$V_s = \left( \frac{\bar{\gamma} RT}{\bar{M}} \right)^{1/2}$$

where $\bar{\gamma}$ is the average specific heat capacity ratio given by:

$$\bar{\gamma} = 1 + \left[ \frac{x}{(\gamma_2 - 1)} + \frac{1-x}{(\gamma_1 - 1)} \right]^{-1}$$

and $\bar{M}$ is the mean molecular weight of the binary gas mixture given by:

$$\bar{M} = (1-x)M_1 + xM_2$$

where x is the mole fraction of a second gas and $M_1$ and $M_2$ are the respective molecular weights of the first and second gases.

To solve for the concentration of a gas component, x, a quadratic equation is formulated from the above equations:

$$x^2 + \left\{ \frac{[A + V_s^2(c-2d)](a-1) + [V_s^2 d - A](b-1)}{V_s^2[(c-d)(b-1) + (d-c)(a-1)]} \right\} x + \frac{(a-1)(V_s^2 d - Ab)}{V_s^2[(c-d)(b-1) + (d-c)(a-1)]} = 0$$

Where:

A=constant=RT a≡$\gamma_2$ and b≡$\gamma_1$, c≡$M_2$ and d≡$M_1$.

x=concentration (mole fraction) of species corresponding to parameters a and c (1−x)=concentration (mole fraction) of species corresponding to parameters b and d $V_s$=is in units of meter/second.

This equation is solved for x using the quadratic formula. Thus, the measurement of the velocity of sound through a binary gas mixture yields the relative amounts of the two gas components.

The principle of acoustic gas analysis has been used in a gas monitoring cell shown in published UK Patent Application GB 2,215,049, the disclosure of which is incorporated by reference herein. In the disclosed cell, ultrasonic pulses are generated by an ultrasonic transducer. The transducer is composed of a piezoelectric material, such as lead zirconate titanate, and is positioned opposite a second transducer. The transit time of sonic pulses between the transducers is measured and used to yield the sound velocity. From the velocity, the composition of the binary mixture is determined.

In the cell of the U.K. patent application, metal gaskets are employed for gas sealing. Because these metal gaskets permit acoustic coupling through the body of the cell, each transducer is supported on an array of mounting pins to minimize acoustic coupling between the transducer and the cell body.

Although the cell of the U.K. application reduces acoustic coupling, there is still sufficient extraneous noise to interfere with the acoustic measurement process. The result is a loss of sensitivity of the cell. Additionally, the cell of the U.K. application operates using ultrasonic frequencies on the order of one megahertz. In general, as sound frequency increases, the attenuation of sound waves also increases. At frequencies in the megahertz range, attenuation of sound in the gas being analyzed is a problem, particularly when attempting to measure high sound absorptive gases, which absorb ultrasound in higher ultrasonic frequency ranges. Because the cell of the U.K. application has a short path length, higher frequencies are required to attain the resolution needed to detect the arriving pulse.

Figure 1:
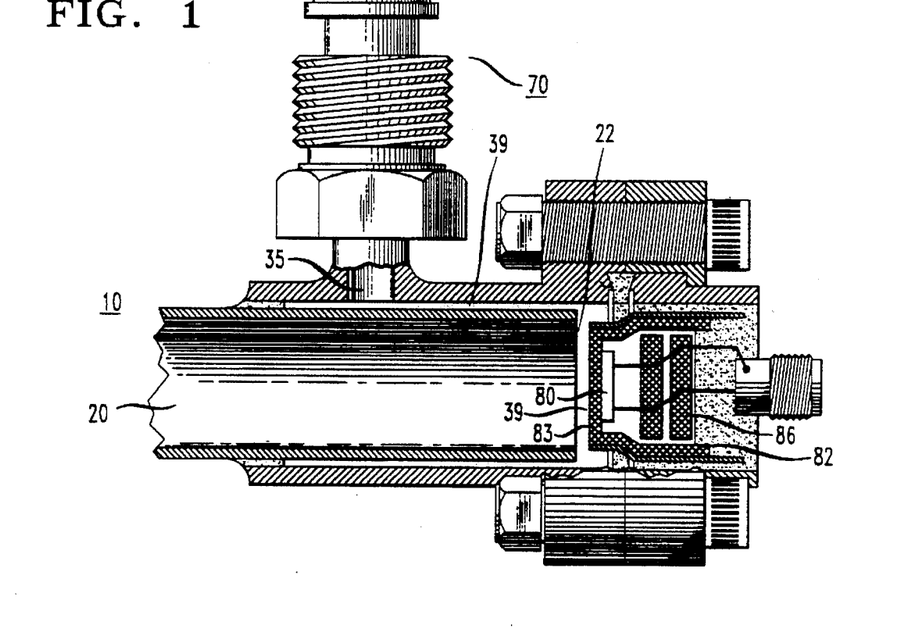
FIG. 1 is an enlarged side view in partial cross-section of a transducer and housing assembled in a prior art acoustic analysis gas cell.

U.S. Pat. No. 5,392,635 to Cadet et al. suggests that the transducer be acoustically isolated to solve the problem of unwanted acoustic coupling. FIG. 1 is a partial cross-section of the acoustic analysis gas cell 10 described in Cadet et al. The transducer 80 is placed opposite the end 22 of conduit 20. Gas flows through a gas port 70, through a passage 35 and a cylindrical gap 39 and into the conduit end 22. The gas passes transducer 80 as it flows into the conduit end 22. As illustrated in FIG. 1, Cadet et al. couple the transducer 80 to a layer of acoustic isolation material 82. The acoustic isolation material 82 is an elastomeric material such as a silicone elastomer. Cadet et al. also propose inserting a layer of this elastomeric material 83 between the transducer 80 and the gaseous mixture to be analyzed. The acoustic isolation provided by Cadet et al. produces a signal-to-noise ratio of at least 4:1. However, since the elastomeric material is exposed to the gas being analyzed, the elastomeric material must withstand exposure to corrosive gas environments. Since elastomers typically degrade when subjected to corrosive gases, the solution offered by Cadet et al. may not be suited for acoustic analysis of all gas mixtures.

In U.S. Pat. No. 5,060,506, a method and apparatus are disclosed for monitoring the ratio of gases in a two-gas mixture using ultrasound. The transmitter used to generate the ultrasonic pulses is excited with a signal having a plurality of successive bursts, each of which includes a preselected number of excitation pulses at the resonant frequency. The initial pulse in each burst is separated from the final pulse in the preceding burst by a quiescent time period of sufficient duration to assure dissipation of transients so that standing waves do not form.

There is a need in the art for improved acoustic cells and methods for analyzing the composition of gas mixtures. More particularly, there is a need in the art for acoustic cells which are compatible with vacuum systems and corrosive gas environments without acoustic coupling of the transducer to the cell body. Additionally, there is a need in the art for an acoustic gas composition analysis cell which operates in a frequency range which permits measurement of a wide variety of gas mixtures.

SUMMARY OF THE INVENTION

The present invention is directed to an acoustic gas composition analysis cell in which the transducers are disposed in stainless steel housings which provide vacuum compatibility and that are resistant to corrosive gas environments. In the cells of the present invention, a transducer generates vibration which is transmitted through the stainless steel housing and into a gas flowing through the cell. Since the stainless steel housings introduce noise into the signal being monitored, it is necessary to reduce the noise in the signal produced by the cell of the present invention. The cell is provided with a sleeve assembly that reduces the noise in the signal, thereby increasing the signal-to-noise ratio to at least about 4:1.

The sleeve assembly is formed around the cell. The sleeve assembly has an outer sleeve and a filler material interposed between the sleeve and the cell body. It is advantageous if the sleeve is an elastomer. The filler material is any material which will acoustically couple to the cell. In this regard it is advantageous if the filler material is physically in contact with the cell. That is, it is advantageous if there is no material such as a gas, interposed between the filler material and the cell. Suitable materials include both solid material such as modeling compounds and liquid materials such as water or alcohol. The filler material is inert with respect to the elastomeric sleeve and the metal body of the cell.

Solid filler materials are preferred because the sound absorption characteristics of these materials varies less with temperature. For example, both modeling compounds and water are suitable fillers at room temperature. But at temperatures above about 45° C., water is no longer able to absorb sound adequately from the cell. This is because the attenuation of ultrasound in water is due to sound absorption from frictional effects. The absorption coefficient (db/mm) decreases with increasing temperature. At these higher temperatures, the modeling compounds absorb sound effectively. Since acoustic cells of the present invention typically operate at temperatures of about 20° C. to about 70° C., filler materials that absorb sound effectively within this range are required.

The transducers employed in the acoustic cell operate in the kilohertz range, reducing attenuation in the gas mixture being analyzed. The cell body employs vacuum seals which permit the use of the cell in line with vacuum equipment.

DETAILED DESCRIPTION

Figure 2:
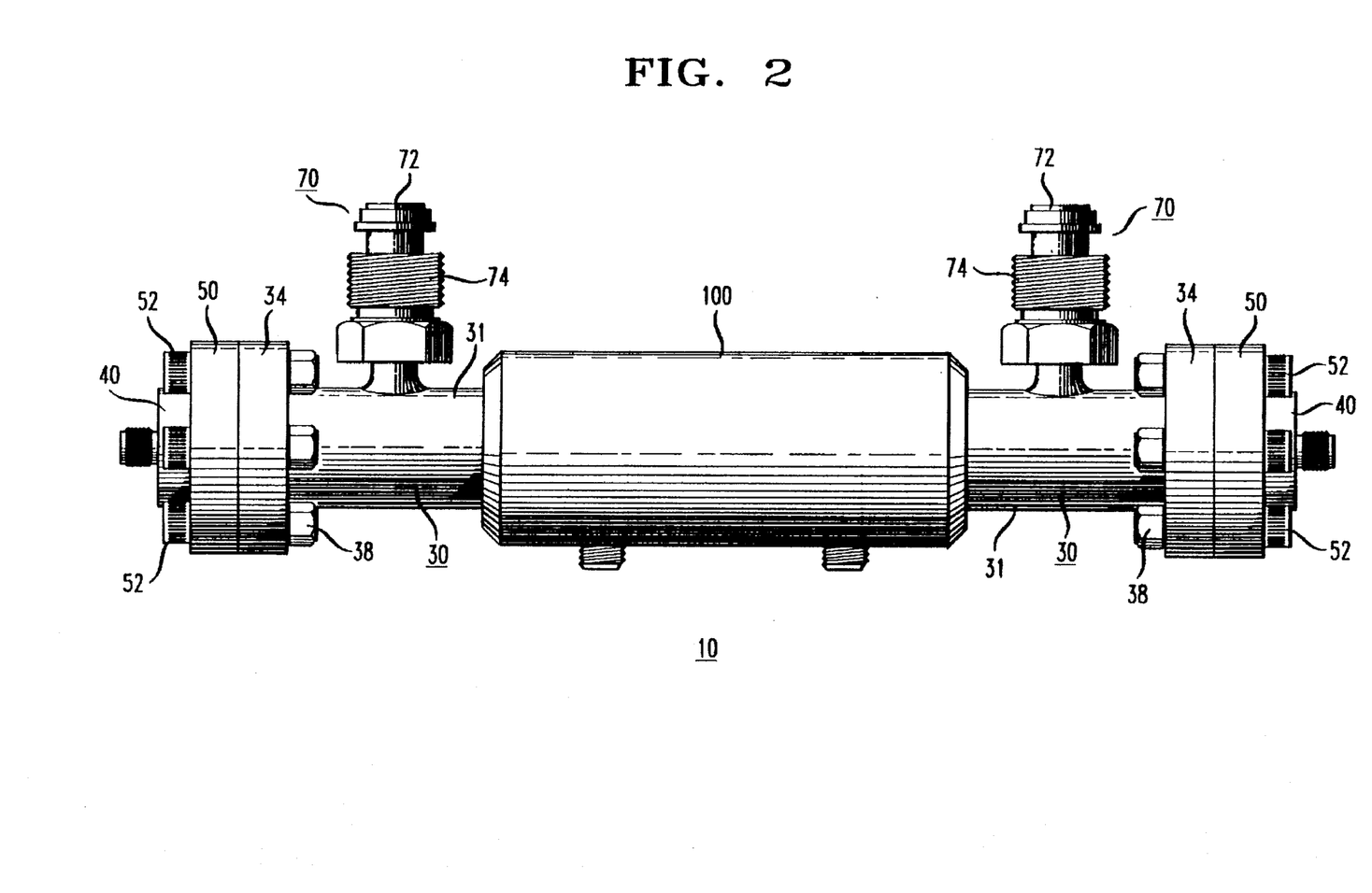
FIG. 2 is a view of an acoustic gas analysis cell according to the present invention.

Turning now to the drawings in detail in which like reference numerals identify like or similar elements in each of the several views, FIG. 2 illustrates an exemplary acoustic gas composition analysis cell according to the present invention. The acoustic gas composition analysis cell 10 includes an electropolished stainless steel cylindrical conduit 20 for propagating sound waves through a gas mixture to be analyzed. 316 stainless steel is an exemplary stainless steel for fabricating conduit 20. First and second transducer housings 40 are coupled adjacent each end of conduit 20 by flange members 30.

Figure 3:
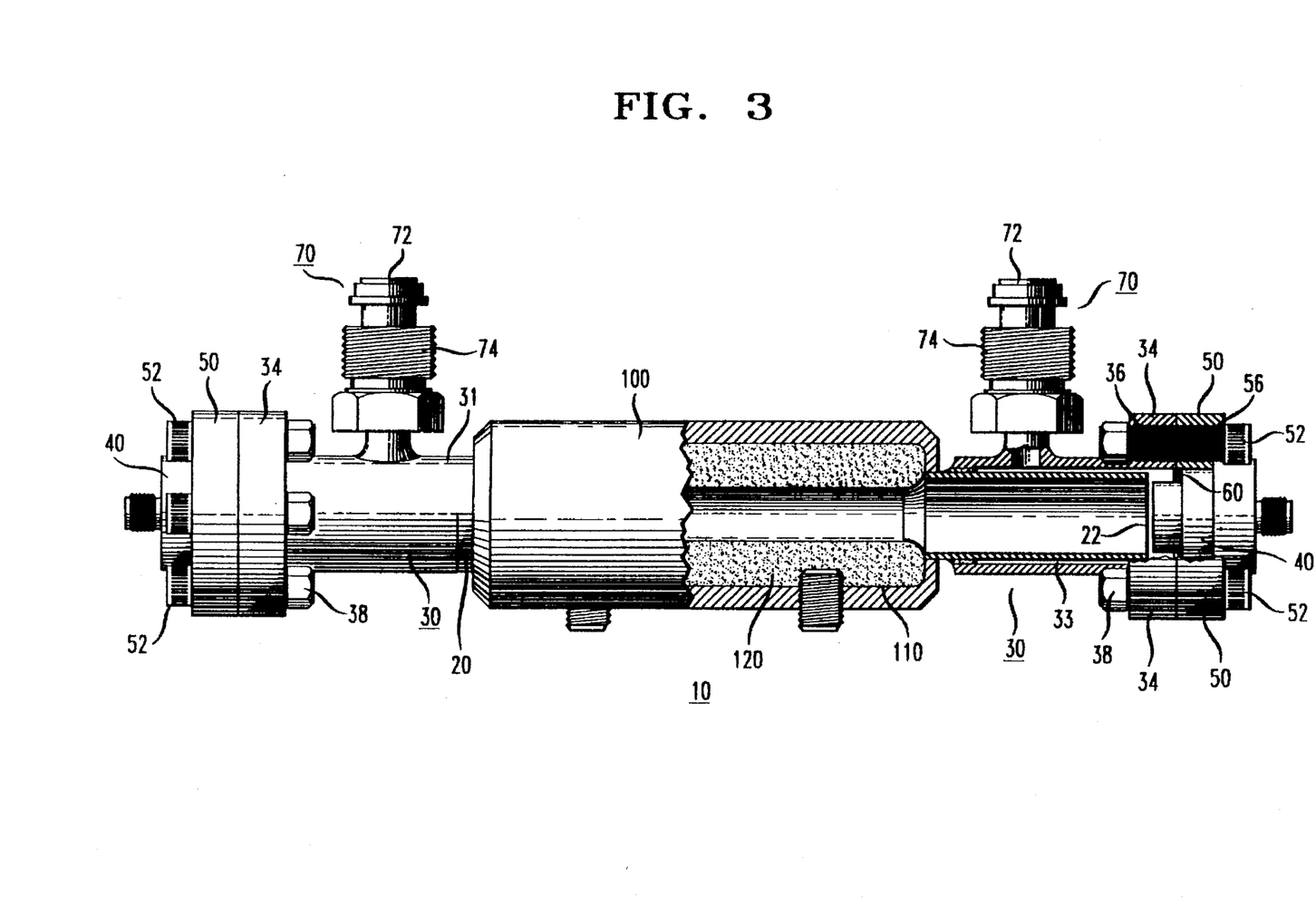
FIG. 3 is a side view in partial cross section of an acoustic gas analysis cell of the present invention.
Figure 4:
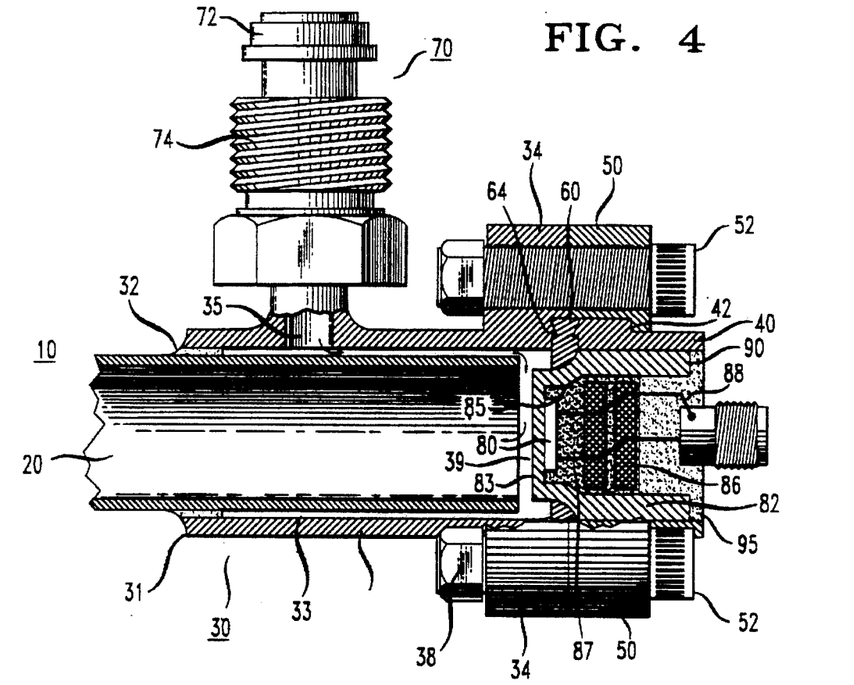
FIG. 4 is an enlarged side view in partial cross-section of a transducer and housing assembled in the acoustic gas analysis cell of the present invention, illustrating gas flow into the cell.

As best seen in FIGS. 3 and 4, flange members 30 each include a hollow cylindrical portion 31 which coaxially surrounds conduit ends 22 to define ring-like spaces 33. At one end, flange member cylindrical portion 31 is affixed to conduit 20 through weld 32. At its other end, flange member cylindrical portion 31 terminates in flange rim 34. The flange rim 34 is provided with a plurality of through-holes 36 for receiving threaded fasteners from a mating flange.

Mating flange 50 is an annular disk which engages transducer housing 40 at housing lip 42 to position the transducer housing adjacent conduit end 22. Flange 50 includes through-holes 56 which align with through-holes 36 of flange rim 34 to receive threaded fasteners 52. Threaded fasteners 52 extend through both sets of through-holes 36 and 56 and are engaged by receiving nuts 38.

Transducer housings 40 must be engaged with flange members 30 in an airtight manner to ensure compatibility of the gas analysis cell with a vacuum system and the corrosive nature of the gasses being analyzed. For this reason, gaskets 60 are made from a metal such as nickel and are positioned between flanges 40 and 50. Gaskets 60 include knife edges 64, best seen in FIG. 4, ensuring a leak-free seal which resists degradation from noxious gases and can withstand vacuum evacuation in the ultrahigh vacuum range. When assembled, transducer housings 40 position transducers 80 adjacent conduit ends 22 to define cylindrical gaps 39. Cylindrical gaps 39 are in fluid communication with the ring-like space 33 between conduit 20 and flange member 30. The use of a separable transducer housing 40 facilitates replacement of the transducer in the event of a transducer failure or the desire to use a transducer having a different resonant frequency.

To enable gas mixtures to flow through the acoustic cell, apertures 35 are provided through the wall of flange member cylindrical portion 31. Gas ports 70 are welded to the flange member wall, enabling fluid communication with space 33 and cylindrical gap 39, best seen in FIG. 4. Each gas port 70 includes a mating member 72 such as a male VCR™ gland engaged within a threaded fastener 74 for facilitating connection to a gas line. In use, one gas port serves as the gas inlet while the other port serves as a gas outlet. As gas flows into a gas port, it passes into ring-like space 33 and cylindrical gap 39 as illustrated by the arrows in FIG. 4. The gas then flows into the conduit 20 through open conduit ends 22. At the opposite end of the cell, the pathway is reversed, and gas exits through the remaining gas port. Advantageously, this gas pathway configuration promotes uniform flow distribution around the transducer, minimizing the dead volume and improving the dynamic response of the device.

The transducer 80 is disposed within a metal housing 82. It is advantageous if the housing is made of a material such as stainless steel, which is resistant to the effects of corrosive gases. The stainless steal housing 82 is coaxially received in transducer housing 40. The end of the metal housing 82 containing the transducer 80 protrudes through the metal gasket 60 and the cylinder gaps 39. The transducer 80 is fixed on the surface 83 of the housing 82 that is adjacent conduit end 22. The transducer 80 is fixed to the surface 83 using conventional adhesives.

The transducer 80 is selected from piezoelectric materials, such as lead-zirconate-titanate crystals. The transducer thickness is chosen to achieve a desired resonant frequency, e.g., a resonant frequency in the kilohertz range. Lead zirconate titanate transducers having resonant frequencies in the range of 50 to 300 kilohertz and, more particularly, 200–215 kilohertz are examples of transducers which can be used in the acoustic cells of the present invention. These frequency ranges are high enough to accurately measure acoustic signal time-of-flight in low molecular weight gases, but not so high as to incur absorption loss in the gas being measured. Both transducers are acoustically matched, i.e., they operate at the same frequency and impedance, thus increasing the signal collected at the receiving transducer. The transducers operate at the resonant frequency which produces the highest output per unit input of electrical signal.

To accurately measure the transit time of sound waves within conduit 20, a shock-absorbing sleeve 100 is wrapped around cylindrical conduit 20. The shock-absorbing sleeve 100 has an inner chamber 110, which is filled with a material 120 that absorbs the noise in the acoustic signal transmitted through the cylindrical conduit 20. The sleeve assembly increases the signal-to-noise ratio between the two transducers 80 to at least about 4:1. It is advantageous if the signal-to-noise ratio between the two transducer 80 is at least about 10:1.

The sleeve is made of a resilient material such as a synthetic elastomer. Examples of suitable materials include Delrin® and Zytel®, both of which are registered trademarks of the Dupont de Nemours Co. Another example of a suitable resin is Lexan®, which is a registered trademark of the General Electric Co. All of these materials are commercially available from a variety of sources.

Figure 6:
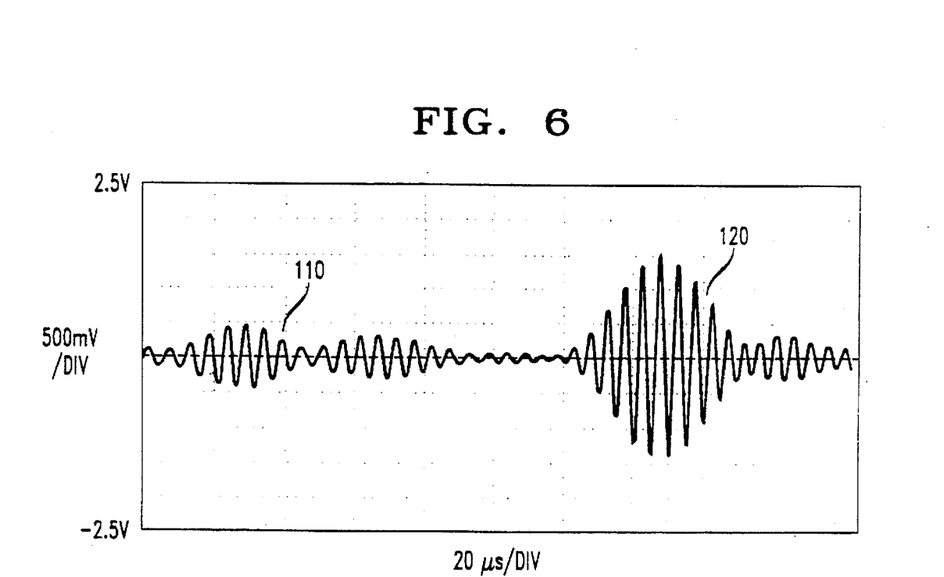
FIG. 6 is an illustration of an acoustic signal over time obtained using an acoustic cell of the present invention without a sleeve containing filler material surrounding the cell.
Figure 7:
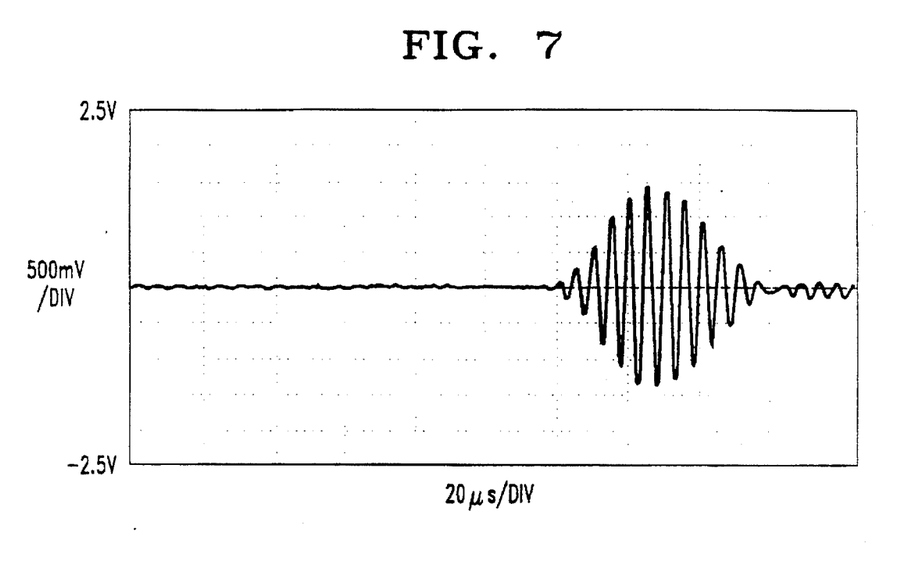
FIG. 7 is an illustration of an acoustic signal over time obtained using an acoustic cell of the present invention at 25° C. wherein clay is the filler material in the sleeve.
Figure 8:
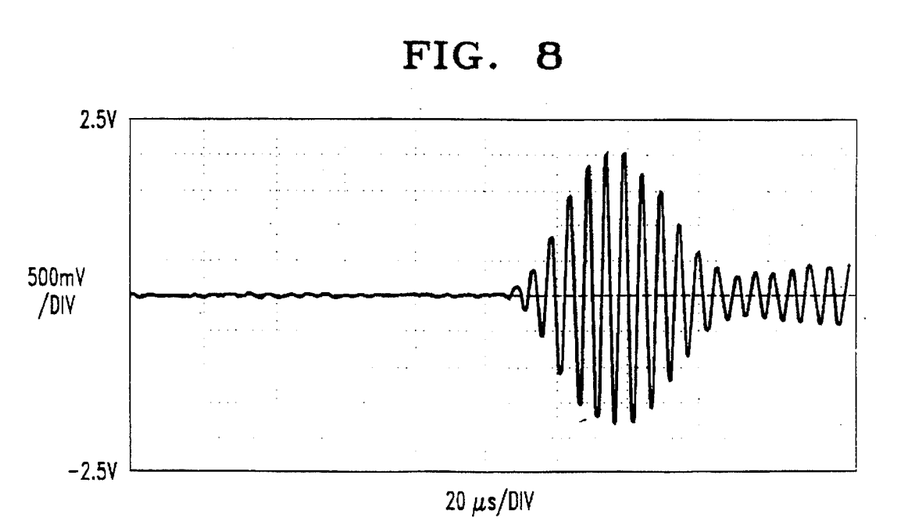
FIG. 8 is an illustration of an acoustic signal in 100% Argon gas over time obtained using an acoustic cell of the present invention wherein clay is the filler material in the sleeve and the temperature of the cell is 50° C.

The sleeve is filled with a material that absorbs the noise generated by the vibration of the stainless steel housing 82 and propagating through the conduit 20. Examples of suitable materials include modeling compounds such as Jolly King and Roma modeling compounds, which are both obtained from Sculpture House of Skillman, N.J. Other solid materials and liquid materials such as mineral oil and glycerol are also contemplated as suitable fillers. The materials must be capable of being distributed evenly in the sleeve, and to couple acoustically to the cell body. In this regard, it is advantageous if pockets of gas do not develop between the filler material and the cell. The materials contemplated as suitable are required to absorb sufficient vibration to reduce the signal-to-noise ratio to an acceptance level. As illustrated in FIG. 6, when the sleeve is filled with air, the signal-to-noise ratio is not reduced by an acceptable amount. Increased power permits sound measurements well above the noise level in the system, i.e., to produce a system with a high signal-to-noise ratio. Such a result is expected if the previously described materials are used as filler. A signal-to-noise ratio of 4:1 is sufficiently high to obtain adequate time-of-flight measurement, with signal-to-noise ratios of greater than 10:1 being exemplary. (as shown in FIGS. 7 and 8).

To effectively absorb acoustic energy radiating from the back surface of the transducer 80, the space behind the transducer 80 is filled with a backing material such as a foam and other sponge-like materials 86. Optionally the backing material is supported by a sound reflecting wall to reflect sound into the backing material, useful for very short time-of-flight acoustic signals. The backing material 86 and space 85 also effectively attenuate extraneous noise transmitted through the transducer housing 40 and sleeve 90 by the remaining cell components, improving the signal to noise ratio. Additionally, the backing material minimizes "ringing" of the transducer, i.e., the undesirable radial vibrations due to even resonances.

Sleeve 90, coupled to a metal sleeve 82 and transducer 80, is assembled with backing material 86 to transducer housing 40 through the use of a fixing agent 95. The fixing agent serves both to mount the components in their proper position within transducer housing 40 and hermetically seal the unit for use with vacuum systems. Additionally, the fixing agent electrically isolates the transducer leads from the cell body. For this reason, the fixing agent can be an epoxy resin selected for compatibility with vacuum systems, such as TORR SEAL®, available from Varian Corporation, Lexington, Mass. The fixing agent 95 assists in attenuating extraneous noise, further promoting acoustic isolation of the transducers.

Transducer leads 87 and 88 pass through backing material 86 and fixing agent 95 to connect the transducers to a signal generating and data processing circuit. Typically, leads 87 and 88 are molybdenum wires formed sufficiently thin so that the effective impedance is much less than that of the transducer crystal to achieve a mismatch loss of energy that would otherwise travel through the leads. In general, the acoustic cell of the present invention may be connected to a variety of signal generators/data processors. The basic characteristics of such systems are that they stimulate a transmitting transducer to generate an acoustic signal and that they record an acoustic signal from a receiving transducer, measuring the transit time of the signal between the transducers. The system processes this information, yielding the sound velocity and concentration of a gas component.

Figure 5:
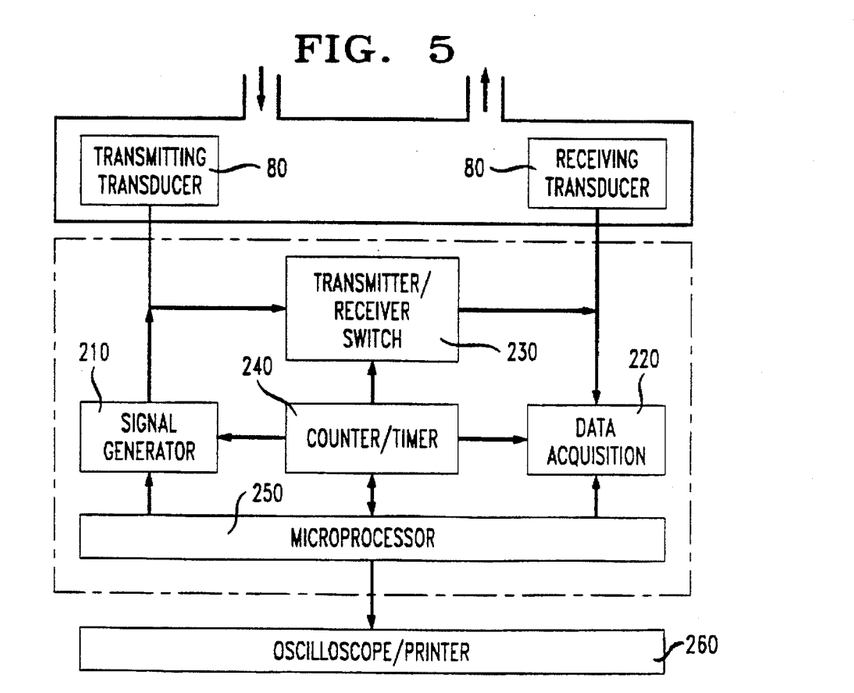
FIG. 5 is a schematic block diagram of the signal generating and data processing circuit used with the acoustic gas analysis cell of FIG. 1.

An example of a preferred signal generation/data processing system which may be employed with the acoustic cells of the invention is illustrated schematically in FIG. 5. The transducers 80 are connected to a signal generator 210, for transmission of ultrasound, and to a data acquisition device 220 for receiving ultrasound. A switch 230 alternates the connection of the transducers between signal generator 210 and data acquisition device 220, permitting each transducer to be used as either a transmitting or a receiving transducer.

Both the signal generator 210 and the data acquisition device 220 are controlled by microprocessor 250 and counter/timer 240. The microprocessor, in addition to controlling the circuit, processes the transit times of the sound waves, using the transducer separation distance to obtain the sound velocity. The microprocessor uses the sound velocity to solve the quadratic equation for the concentration of a gas mixture constituent. The results of that computation are then transmitted to oscilloscope/printer 260. The microprocessor may further be connected to a feedback loop which controls the flow of the gas constituent in response to the measured concentration.

An example of a signal generator/receiver system which may be employed with the acoustic cells of the invention is Panametrics Inc. Model 5055PR. In this device, the transmitting transducer is energized by a trigger-type, pulse-forming circuit that produces short pulses. The received pulses are amplified, shaped, and then used to synchronize the original pulse-forming circuit.

A further example of a system used to generate and receive pulses which may be used with the acoustic cells of the invention is Panametrics Inc. Model CP6068. This system drives the transmitter with a binary phase-encoded signal, typically 4 to 20 cycles in length. The received signal is digitized using a "flash" analog to digital (A/D) converter and determines the transit time by correlating the encoded transmitted signal with the digitized received signal.

The signal-to-noise ratio is unacceptably high if the acoustic cell is used without the previously described sleeve assembly. To obtain the signal illustrated in FIG. 6, argon at 25° C. was flowed through a cell as previously described at a flow rate of 200 sccm. The cell did not have a sleeve assembly thereon. As illustrated by FIG. 6, the signal-to-noise ratio in the signal generated by the acoustic cell was unacceptably high. The noise portion of the signal is indicated as 110 in FIG. 6 and the signal portion of the signal is indicated as 120. The same conditions were used to generate a signal in an acoustic cell with a sleeve assembly thereon. The sleeve assembly was a Delrin sleeve filled with Roma clay obtained from Sculpture House, Inc. of Skillman, N.J. As illustrated in FIG. 7, the signal-to-noise ratio was substantially reduced from the signal-to-noise ratio of the signal depicted in FIG. 6 due to the presence of the clay-filled sleeve on the cell.

Using the shock-absorbing sleeve of the present invention, a significant reduction in the signal-to-noise ratio was obtained even at high temperature. As illustrated in FIG. 8, the signal-to-noise ratio of a signal generated using an acoustic cell with the previously described sleeve assembly was reduced even when the temperature of the gas flowing through the acoustic cell was 50° C.

Figure 9:
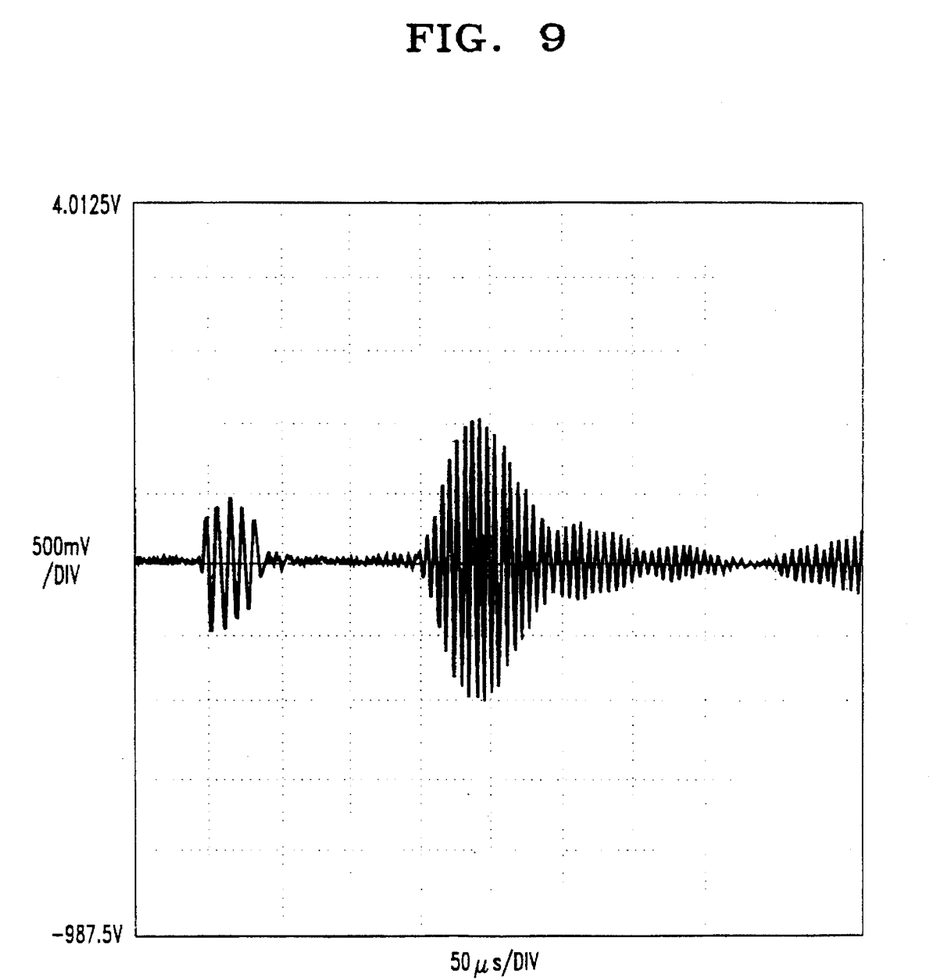
FIG. 9 is an illustration of an acoustic signal in 100% helium over time using an acoustic cell of the present invention wherein clay is the material in the vibration-absorbing sleeve on the cell.

FIG. 9 illustrates the signal obtained from an acoustic cell of the present invention with a sleeve thereon as previously described. Helium gas at a temperature of 42° C. flowed through the cell as the information was obtained. FIG. 9 demonstrates that, even in a low molecular weight gas in which the speed of sound is very fast and in which the signal is not as quickly attenuated as in higher molecular weight gasses, a high signal-to-noise ratio is obtained using the cell of the present invention, thereby permitting reliable measurement regardless of time of light.

Because the velocity of sound in a gas is also dependent upon the gas temperature, for greatest accuracy it is important to conduct the sound measurement in a constant temperature environment. To this end, the acoustic cell and gas lines can be positioned within a standard exhausted gas cabinet which provides constancy in the temperature of the system to within ±0.1° C. Alternatively, a thermocouple can be positioned within the acoustic cell and the gas temperature can be input to the microprocessor along with the transit time for determining the gas composition.

In use, the acoustic gas analysis cell 10 is coupled to a gas flow line through gas ports 70. To calibrate the system, the distance between the transducers is accurately determined using inert gases such as argon and helium. The transmitting transducer launches a pulse of sound at the resonant frequency which passes through the gas contained within conduit 20. For lead zirconate titanate (PZT) transducers, this resonant frequency is approximately 100 kHz to 250 kHz depending upon the thickness and geometry of the PZT material.

The transmitted pulse is detected by the receiving transducer which is axially aligned with the transmitting transducer. Because the transducers operate at the same frequency and are acoustically matched, either transducer 80 in the acoustic cell of FIG. 2 can be selected as the transmitting transducer, the remaining transducer being used as the receiving transducer. To improve measurement accuracy, the transducers can be operated in an alternating mode, i.e., the transducers alternately send and receive signals. Using this mode of operation, the transit time of the ultrasonic pulses is measured both with and against the direction of gas flow. The velocity is the average of the measured upstream and downstream velocities.

Using the velocity, the composition of the gas mixture is obtained. The concentration of a particular gas component is calculated by solving for x in the above quadratic equation. A list of coefficients used to solve the quadratic equation for various binary gas mixtures is given in Table 1 below:

| List of Coefficients for Quadratic Formulation | | | | | |
|---|---|---|---|---|---|
| Binary Gas | a | b | $c \times 10^{-3}$ | $d \times 10^{-3}$ | A |
| 1.) $AsH_3/H_2$ | 1.269 | 1.405 | 77.946 | 2.01594 | 2,478.909 |
| 2.) $PH_3/H_2$ | 1.289 | 1.405 | 33.9978 | 2.01594 | 2,478.909 |
| 3.) $Ar/He$ | 1.669 | 1.630 | 39.948 | 4.0026 | 2,478.909 |
| 4.) $NH_3/H_2$ | 1.304 | 1.405 | -17.031 | 2.01594 | 2,478.909 |
| 5.) $SiH_4/H_2$ | 1.241 | 1.405 | 32.118 | 2.01594 | 2,478.909 |
| 6.) $H_2Se/H_2$ | 1.314 | 1.405 | 80.976 | 2.01594 | 2,478.909 |

-continued

List of Coefficients for Quadratic Formulation

| Binary Gas | a | b | c × 10⁻³ | d × 10⁻³ | A |
|---|---|---|---|---|---|
| 7.) HCl/$H_2$ | 1.399 | 1.405 | 36.461 | 2.01594 | 2,478.909 |
| 8.) $N_2$/$H_2$ | 1.407 | 1.405 | 14.0067 | 2.01594 | 2,478.909 |
| 9.) $CH_4$/$H_2$ | 1.305 | 1.405 | 16.043 | 2.01594 | 2,478.909 |
| 10.) $NH_3$/$N_2$ | 1.307 | 1.407 | 17.031 | 14.0067 | 2,478.909 |
| 11.) $GeH_4$/$H_2$ | 1.227 | 1.405 | 76.63 | 2.01594 | 2,478.909 |
| 12.) TMI/$H_2$ (trimethyl indium) | 1.10 | 1.403 | 159.925 | 2.01594 | 3,102.481 |
| 13.) TMG/$H_2$ (trimethyl gallium) | 1.10 | 1.403 | 114.825 | 2.01594 | 3,102.481 |
| 14.) $SiCl_4$/$O_2$ | 1.627 | 1.414 | 169.9 | 32 | 3,102.481 |
| 15.) $GeCl_4$/$O_2$ | 1.097 | 1.414 | 214.4 | 32 | 3,102.481 |

The acoustic cells and methods described herein find application in various chemical vapor deposition processes. Deposition of glasses for fiber optic preform fabrication is an example of such a chemical vapor deposition process. Mixtures of silicon tetrachloride, $SiCl_4$, with oxygen and mixtures of germanium tetrachloride, $GeCl_4$, with oxygen are used to build up glass layers on the inside wall of a rotating silica tube to produce a graded index profile. For multimode fibers, the deposited layers become the core and the silica tube becomes the cladding. Further process parameters can be found in MacChesney et al., *Proc. IEEE*, Vol. 62 (1974), p. 1280, the disclosure of which is incorporated by reference herein. The acoustic cells are used to control the relative proportions of $SiCl_4$ and oxygen and $GeCl_4$ and oxygen.

The acoustic cells and methods of the present invention can be used individually for measurement of binary gas mixtures, or in series and parallel combinations for measurement of gas mixtures having more than two constituents. For example, an acoustic cell may be placed in a gas line to measure a first binary gas mixture. This binary mixture may then be further mixed with a third gas and a second acoustic cell may be used to control the relative proportions of the binary gas mixture and the third gas. The third gas may be a single gas or may itself be a binary gas mixture, the relative concentrations of its components having been controlled by an acoustic cell upstream of the later mixing point.

While the foregoing invention has been described with respect to the preferred embodiments, it is understood that various changes and modifications such as those suggested above, but not limited thereto, may be made without departing from the scope of the claims.

The invention claimed is:

1. An acoustic cell for determining the composition of a gas mixture comprising:

a hollow conduit for containing a gas mixture to be analyzed, said conduit having first and second ends;

a first transducer housing sealingly engaged with said first end of the conduit, said first transducer housing supporting a first transducer, the first transducer housing being made of a metal;

a second transducer housing sealingly engaged with said second end of the conduit, said second transducer housing supporting a second transducer, the second transducer housing being made of metal, a sound-absorbing sleeve assembly surrounding the conduit;

a first gas port coupled to said first end of the conduit; and a second gas port coupled to said second end of the conduit;

wherein sound-absorbing sleeve assembly provides an acoustic cell that produces a signal-to-noise ratio of at least 4:1.

2. An acoustic cell as recited in claim 1 wherein said first and second transducers resonate at a frequency between 50 and 300 kilohertz.

3. The acoustic cell of claim 1 wherein the shock absorbing sleeve assembly has a configuration that permits the sleeve to surround the conduit, wherein the sleeve has an inner portion that is in sufficient contact with the conduit to permit transmission of vibration from the conduit to the sleeve.

4. The acoustic cell of claim 3 wherein the sleeve assembly has a thickness defined by the inner portion and an outer portion, wherein a hollow portion filled with a sound-absorbing material is disposed within the thickness.

5. The acoustic cell of claim 4 wherein the outer portion is an elastomeric sleeve and the inner portion is a sound-absorbing material.

6. The acoustic cell of claim 5 wherein the sound-absorbing material is modeling compound.

7. The acoustic cell of claim 5 wherein the vibration-absorbing material produces a signal-to-noise ratio of at least 10:1.

* * * * *